US008598082B2

(12) United States Patent
Hewlett et al.

(10) Patent No.: US 8,598,082 B2
(45) Date of Patent: Dec. 3, 2013

(54) **MATERIALS AND METHODS FOR CONTROLLING NEMATODES WITH *PASTEURIA* SPORES IN SEED COATINGS**

(75) Inventors: Thomas E. Hewlett, High Springs, FL (US); John P. Waters, Lake City, FL (US); Charles S. Barmore, Gainesville, FL (US)

(73) Assignee: Pasteuria Biosicence, Inc., Alachua, FL (US)

( * ) Notice: Subject to any disclaimer, the term of this patent is extended or adjusted under 35 U.S.C. 154(b) by 361 days.

(21) Appl. No.: 12/642,041

(22) Filed: Dec. 18, 2009

(65) Prior Publication Data

US 2010/0160160 A1 Jun. 24, 2010

Related U.S. Application Data

(60) Provisional application No. 61/139,304, filed on Dec. 19, 2008.

(51) Int. Cl.
*A01N 63/00* (2006.01)

(52) U.S. Cl.
USPC .......................................................... 504/117

(58) Field of Classification Search
None
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,339,456 | A | 7/1982 | Rushing |
| 4,372,080 | A | 2/1983 | Rushing |
| 4,383,391 | A | 5/1983 | Thomas et al. |
| 4,465,017 | A | 8/1984 | Simmons |
| 4,634,587 | A | 1/1987 | Hsiao |
| 4,735,015 | A | 4/1988 | Schmolka |
| 4,759,945 | A | 7/1988 | Nemecel et al. |
| 5,080,925 | A | 1/1992 | Kouno |
| 5,094,954 | A | 3/1992 | Previc et al. |
| 5,107,787 | A | 4/1992 | Kouno |
| 5,248,500 | A | 9/1993 | Ayanaba |
| 5,300,127 | A | 4/1994 | Williams |
| 5,328,942 | A | 7/1994 | Akhtar et al. |
| 5,389,399 | A | 2/1995 | Bazin et al. |
| 5,554,445 | A | 9/1996 | Struszczyk et al. |
| 5,580,554 | A | 12/1996 | Keith |
| 5,593,668 | A | 1/1997 | Nishimuta et al. |
| 5,622,003 | A | 4/1997 | Narayanan |
| 5,661,103 | A | 8/1997 | Harms et al. |
| 5,791,084 | A | 8/1998 | Kohno et al. |
| 5,834,447 | A | 11/1998 | Phillion et al. |
| 5,849,320 | A | 12/1998 | Turnblad et al. |
| 5,876,739 | A | 3/1999 | Turnblad et al. |
| 5,882,713 | A | 3/1999 | Eskins et al. |
| 5,891,246 | A | 4/1999 | Lund |
| 5,918,413 | A | 7/1999 | Otani et al. |
| 5,939,356 | A | 8/1999 | Wellinghoff |
| 5,989,543 | A | 11/1999 | Romulo et al. |
| 6,110,904 | A | 8/2000 | Warrior et al. |
| 6,808,917 | B1 * | 10/2004 | Johnson ..................... 435/252.4 |
| 6,919,197 | B2 | 7/2005 | Gerber et al. |
| 7,067,299 | B2 | 6/2006 | Gerber et al. |
| 7,213,367 | B2 | 5/2007 | Wertz et al. |
| 2004/0137600 | A1 | 7/2004 | Gerber et al. |

FOREIGN PATENT DOCUMENTS

| | | |
|---|---|---|
| EP | 0 217 378 | 4/1987 |
| EP | 0623284 | 11/1994 |
| JP | 03-198703 | 8/1991 |
| JP | 2000-095627 | 4/2000 |
| JP | 2004-210645 | 7/2004 |
| JP | 2008-189658 | 8/2008 |
| WO | WO 91-02051 | 2/1991 |
| WO | WO 00/51435 A1 | 9/2000 |
| WO | WO-01/11017 * | 2/2001 |
| WO | WO 2007/149817 | 12/2007 |
| WO | WO-2007149817 * | 12/2007 |
| WO | WO 2010/030554 | 3/2010 |

OTHER PUBLICATIONS

Stirling, G.R., "Biological control of *Meloidogyne javanica* with *Bacillus penetrans*," *Phytopathology*, 1984, pp. 55-60, vol. 74.
Gomathi et al. "Effective dose and methods of delivery of *Pastueria penetrans* against root-knot nematode in Brinjal" *Ann. Pl. Protec. Sci.*, 2006, pp. 452-455, vol. 14, No. 2.

* cited by examiner

*Primary Examiner* — Alton Pryor
(74) *Attorney, Agent, or Firm* — Saliwanchik, Lloyd & Eisenschenk

(57) ABSTRACT

The subject invention provides novel and advantageous materials and methods for controlling phytopathogenic and/or soil-dwelling nematodes by attaching an effective amount of *Pasteuria* spores to a seed and delivering the seeds to the situs of nematodes.

25 Claims, 3 Drawing Sheets

MATERIALS AND METHODS FOR CONTROLLING NEMATODES WITH *PASTEURIA* SPORES IN SEED COATINGS

CROSS-REFERENCE TO A RELATED APPLICATION

The present application claims the benefit of U.S. Provisional Application Ser. No. 61/139,304, filed Dec. 19, 2008, which is hereby incorporated by reference in its entirety, including all figures, tables or drawings.

BACKGROUND OF INVENTION

Crop losses due to plant parasitic nematodes are estimated to exceed $100 billion. Preventing this damage represents a significant challenge. With the impending loss of the fumigant methyl bromide, there is insufficient time to develop and register new synthetic compounds for nematode control. Therefore, other options are needed.

Phytopathogenic nematodes are particularly difficult to control because they are covered with a thick, impermeable cuticle, or outer covering, and have very few sensory neurons. Since many pest control compounds operate as neurotoxins, the low number of neurons exposed by phytopathogenic nematodes decreases the effective target area for nematicidal compounds and has resulted in the development of nematicidal compounds with extremely high neurotoxic properties.

Furthermore, because phytopathogenic nematodes are found in soil or plant roots, exposing the phytopathogenic nematodes to control agents is difficult to achieve and puts the water table at risk of contamination from these toxic compounds. The use of nematicides based on neurotoxins has been demonstrated to contaminate both ground and surface water. Consequently, many of these compounds are being removed from the market for public health reasons.

Fumigation of soil prior to planting is a popular method for controlling nematodes. One of the most popular fumigants, methyl bromide, is slated for removal from use because of its ozone destroying properties. Furthermore, this practice of soil fumigation kills organisms in soil indiscriminately and runs the risk of eliminating beneficial microbes as well as disease-causing organisms. Therefore, an effective nematicide with benign environmental effects is urgently needed.

*Pasteuria* was first described in 1888 by Metchnikoff (Annales de l'Institut Pasteur 2:165-170) as a parasite of water fleas. Subsequently, Cobb described a *Pasteuria* infection of the nematode *Dorylaimus bulbiferous* ($2^{nd}$ ed. Hawaiian Sugar Planters Assoc., Expt. Sta. Div. Path. Physiol. Bull. 5:163-195, 1906).

The life cycle of the bacteria involves a stage when endospores bind to the cuticle of the nematodes in soil. *P. penetrans* then proliferates within the nematode body and passes through several morphological phases, including mycelial structures and thalli, culminating in the development of new endospores. Endospores are released when the nematode body lyses.

Growth of the bacteria within the nematode body reduces or eliminates the production of eggs by the nematode, severely restricting the rate of nematode reproduction. Economic damage to the host crop normally is inflicted by the first generation progeny of nematodes and is prevented by *Pasteuria* through lowering the concentration of progeny nematodes in the plant root zone.

Although the use of *Pasteuria* to control nematodes has been previously proposed, a number of factors, including sub-optimal delivery options have limited the use of this nematode control strategy. Conventional methods for controlling nematodes using *Pasteuria* strains include applying the bacteria to the plant and soil in free form (e.g. Stirling G. R. 1984. "Biological control of *Meloidogyne javanica* with *Bacillus penetrans*", Phytopathology, 74:55-60) or in solid and liquid formulation (e.g. U.S. Pat. No. 5,248,500). However, despite the highly selective effectiveness of the bacteria on the phytopathogenic nematodes, they need to be in contact with the nematodes in order to produce the nematocidal effect. When applied directly to the soil, a large amount of the bacteria is required and they have to be mixed well with the soil, which substantially increases the cost of using the bacteria.

While various biocontrol methods using *Pasteuria* bacteria are known, there still remains a need for an improved approach for using these bacteria to effectively control nematodes. Therefore, the subject invention provides novel methods for controlling phytopathogenic nematodes that attack plants.

BRIEF SUMMARY OF THE INVENTION

The subject invention provides novel and advantageous materials and methods for controlling phytopathogenic nematodes and/or other soil-dwelling nematodes by delivering to the soil a composition comprising an effective amount of *Pasteuria* spores that are attached to a seed.

Upon planting the seeds of the subject invention, the *Pasteuria* spores are transferred to the soil surrounding the seed. It has been found that, when the method of the subject invention is practiced, the spores then attach to, infect, grow in, re-sporulate in, reduce the fecundity of, and/or kill phytopathogenic nematodes and/or other soil-dwelling nematodes in the vicinity of the seed and, ultimately, any plant that develops from the seed.

The method of the subject invention can be used for controlling or reducing harm caused by nematode infection, and, in preferred embodiments, can enhance seed emergence, plant growth and plant health.

One aspect of the present invention provides a method for nematode control by delivering to the situs of a nematode infection an effective amount of *Pasteuria* spores attached to plant seeds.

The *Pasteuria* spores of the present invention can be applied to seeds as unformulated spores or as a formulated liquid or solid composition, slurry of particles, or emulsion. In one embodiment, *Pasteuria* spores are formulated into a liquid composition. In another embodiment, *Pasteuria* spores are formulated into a solid composition. Suitable solid carriers include but are not limited to solid polymeric matrices, particles, granules and powders. In one embodiment, the solid carrier is made up of granules.

In preferred embodiments, the *Pasteuria* composition is associated with the seeds by coating, spraying, or otherwise attaching to, contacting, or mixing the seeds with a *Pasteuria* composition. In one embodiment, the *Pasteuria* composition is applied by coating at least part of the surface area of the seed with the *Pasteuria* composition.

In one embodiment, the plant seed is first treated with an adherent that can adhere to the *Pasteuria* spores and/or a composition containing the spores. The adherent can be, for example, a glue and/or one or more polymers or copolymers. Examples of adherents include, but are not limited to, glues (such as ELMERS™ glue); polyvinyl acetates; silicone materials; and natural inorganic materials such as silica gel and clay.

Another aspect of the subject invention provides a seed having at least part of its surface coated with a *Pasteuria* composition, wherein the *Pasteuria* composition comprises an effective amount of *Pasteuria* spores for nematode control.

DETAILED DISCLOSURE

Figure 1:
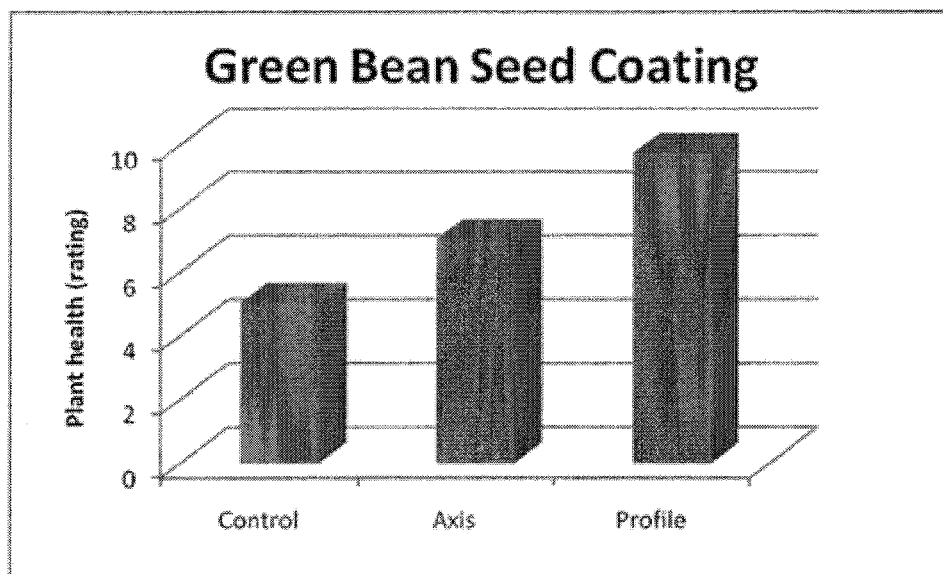
FIG. 1 shows the health of plants grown from seeds coated with *Pasteuria* for nematode control.

The present invention provides materials and methods for efficient control of phytopathogenic nematodes and/or other soil-dwelling nematodes by utilizing plant seeds coated with *Pasteuria* spores.

Advantageously, *Pasteuria* produce endospores that have the unique and useful property of being able to attach to, infect, grow in, re-sporulate in, reduce the fecundity of, and/or kill phytopathogenic nematodes and other soil-dewelling nematodes.

One aspect of the present invention provides methods for nematode control by delivering, to the situs of a nematode infection, an effective amount of a *Pasteuria* composition as a plant seed coating.

*Pasteuria* delivered as seed coatings according to the subject invention can reduce the ability of nematodes to infect plants. As a result, in preferred embodiments, the subject treatment method is capable of controlling or reducing harm caused by nematode infection, thereby enhancing seed emergence, plant growth and/or plant health.

*Pasteuria* spores of the present invention can be produced in vivo within living hosts (e.g. Verdeho, S., and R. Mankau, 1986, *Journal of Nematology,* 18:635), or in vitro without the presence of living host tissues (e.g. U.S. Pat. No. 5,094,954). In a specific embodiment, *Pasteuria* spores of the present invention are produced using fermentation techniques described in, for example, U.S. Pat. Nos. 7,067,299 and 6,919,197.

Various *Pasteuria* species (*Pasteuria* spp.) are suitable for use for nematode control. In one embodiment, the active ingredient comprises an effective amount of *Pasteuria* penetrans spores for controlling root-knot nematodes. In other embodiments, the active ingredient comprises an effective amount of *Pasteuria* spores selected from *Pasteuria ramose, Pasteuria thornea, Pasteuria usage, Pasteuria nishizawae,* any combination thereof, as well as new nematicidally species that will be identified.

The nematicidally-effective amount of *Pasteuria* spores will vary, depending upon factors including, but not limited to, the plant species, the surface area of the seed, the type of carrier, presence or absence of other active ingredients, the method of formulation, the route of delivery, the *Pasteuria* species, the target nematode species, and the seriousness of the nematode infection or damage to the plant(s).

"A nematicidally effective amount" as used herein refers to an amount of *Pasteuria* spores capable of killing, controlling, or infecting nematodes; retarding the growth or reproduction of nematodes; reducing a nematode population; and/or reducing damage to plants caused by nematodes. In general, the effective amount of spores range from about $1\times10^5$ to $1\times10^{12}$ (or more) spores/seeds. Preferably, the spore concentration is about $1\times10^6$ to about $1\times10^9$ spores/seed.

An "active ingredient" as used herein refers to a substance that is useful for killing, controlling, or infecting nematodes or other pests; and/or retarding the growth or reproduction of nematodes or other pests; reducing nematode or pest populations, and/or reducing damage to plants caused by nematodes or other pest(s).

An "agriculturally beneficial ingredient" as used herein refers to a substance that is useful or productive in agriculture settings, for example, useful for controlling a disease, a pest (including for example an insect, a parasite, a virus, a fungus, a bacterium) and/or a weed; useful for promoting the quantity and quality of plant growth, plant health, seed emergence, plant reproduction and/or fruit growth. Agriculturally beneficial ingredients include but are not limited to pesticides, herbicides, fungicides, fertilizers, and bio-control agents.

An "inert or inactive ingredient" as used herein refers to a substance that aids in the operation or improves the effectiveness of an agricultural formulation or composition. Inert or inactive ingredients include but are not limited to a carrier, an adherent, a dispersant, a surfactant, a liquid dilutant, a binder, a filler agent, a solvent, a wetting agent, a sticker, an emulsifier, a nutrient, a surfactant, a penetrant, a foaming agent, a solubilizer, a spreader, and a buffer agent.

In certain embodiments, the *Pasteuria* composition is applied to the seeds by coating, spraying, attaching to, contacting, or mixing the seeds with the *Pasteuria* composition. In one embodiment, the *Pasteuria* composition is attached to the seed by coating at least part of the surface area of the seed with the *Pasteuria* composition.

In a specific embodiment, the *Pasteuria* composition is applied to the seed by a) impregnating a solid carrier with the *Pasteuria* composition to obtain a *Pasteuria*-carrier mixture; and b) contacting the seed with the *Pasteuria*-carrier mixture.

Another aspect of the invention provides seeds treated with the subject *Pasteuria* composition. One embodiment provides seeds having at least part of the surface area coated with the *Pasteuria* composition. In a specific embodiment, the *Pasteuria* treated seeds have a spore concentration from about $10^6$ to about $10^9$ spores per seed. The seeds may also have more spores per seed, such as, for example $1\times10^{10}$, $1\times10^{11}$ or $1\times10^{12}$ spores per seed.

Formulation of *Pasteuria* Composition

The *Pasteuria* of the present invention can be delivered to seeds as unformulated spores or as a formulated liquid or solid composition, slurry of particles, or emulsion.

In one embodiment, the *Pasteuria* spores are formulated into a liquid composition. Endospores are suspended in a medium buffered to maintain the desired pH. Preferably, the pH is less than about 6.0, more preferably the pH is less than about 5.5 and, most preferably, the pH is between about 3.0 and about 5.0. Buffer systems that can be used include, but are not limited to, potassium hydrogen phthalate, acetic acid, succinic acid and citric acid. Agents that can be used to acidify the culture medium include, but are not limited to, hydrochloric acid, sulfuric acid, acetic acid, and other organic acids.

In another embodiment, the *Pasteuria* composition may optionally comprise one or more amino acids, salts, carbohydrates, vitamins, and other supporting nutrients. In a specific embodiment, the *Pasteuria* suspension may comprise one or more of the following components: glucose, NaCl, yeast extract, $NH_4H_2PO_4$, $(NH_4)_2SO_4$, glycerol, valine, L-leucine, L-glutamine, L-alanine, L-valine, L-tyrosine, L-tryptophan, lactic acid, propionic acid, succinic acid, malic acid, citric acid, KH tartrate, vitamin solution, mineral solution, xylose, lyxose, and lecithin. In another specific embodiment, the suspension may comprise one or more of the following components: lactic acid, propionic acid, succinic acid, malic acid, citric acid, tartaric acid, and yeast extract.

In one embodiment, *Pasteuria* spores are formulated into a solid composition. The solid suspension can be prepared by mixing *Pasteuria* spores or a liquid *Pasteuria* suspension with a solid carrier. In one embodiment, the solid composition is obtained by impregnating the solid carrier with the spore suspension, and subsequently drying the solid composition.

Suitable solid carriers include, but are not limited to, solid polymeric matrices, particles, granules and powders. In one embodiment, the solid carrier is made up of granules. In one embodiment, the subject composition is formulated as an emulsion; slurry of particles in an aqueous medium (e.g., water); wettable powders; wettable granules (dry flowable); or dry granules. In a specific embodiment, the solid carrier is diatomaceous earth granules from AXIS® and/or greens-grade clay granules from PROFILE®.

The subject *Pasteuria* composition can be formulated as, for example, a liquid suspension, a solid composition, or aqueous slurry. The concentration of the active ingredient can range from about 0.5% to about 99% by weight (w/w), about 5% to about 80%, about 10% to about 75%, about 15% to about 70%, about 20% to about 65%, about 25% to about 60%, about 30% to about 55%, about 35% to about 50%.

In another embodiment, the subject composition is formulated as a *Pasteuria*-granule mixture. The amount of *Pasteuria* spores to granules can range from about $1\times10^6$ to about $7\times10^8$ spores/g granules, about $5\times10^6$ to about $5\times10^8$ spores/g granules, about $1\times10^7$ to about $1\times10^8$ spores/g granules, or about $3\times10^7$ to about $5\times10^7$ spores/g granules.

In a specific embodiment, the granule composition is obtained by mixing about 3-5 ml of a $2\times10^7$ spores/ml *Pasteuria* spore suspension with about 2 g granules. In a further specific embodiment, the granule composition is obtained by mixing about 5 ml of the spore suspension with about 2 g AXIS® granules. In another further specific embodiment, the granule composition is obtained by mixing about 3 ml of the spore suspension with about 2 g PROFILE® granules.

Particles of the solid composition can be of any size capable of attaching *Pasteuria* spores to a plant seed.

In a further embodiment, the *Pasteuria* composition further comprises one or more conventional inactive or inert ingredients, including, for example, adherents, dispersants, surfactants, liquid dilutants, binders, filler agents, solvents, wetting agents, stickers, emulsifiers, nutrients and buffer agents.

Conventional inactive or inert ingredients include, but are not limited to: conventional sticking agents; dispersing agents such as methylcellulose (METHOCEL™ A15LV or METHOCEL™ A15C, for example, serve as combined dispersant/sticking agents for use in seed treatments); polyvinyl alcohol (e.g., ELVANOL™ 51-05); lecithin (e.g., YELKINOL™ P), polymeric dispersants (e.g., polyvinylpyrrolidone/vinyl acetate PVPIVA S-630); thickeners (e.g., clay thickeners such as Van Gel B to improve viscosity and reduce settling of particle suspensions); emulsion stabilizers; surfactants; antifreeze compounds (e.g., urea), dyes, colorants, and the like. Additional inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

In one embodiment, an adherent is used to facilitate attachment of the spores to the seeds. The adherent attaches the spores or the *Pasteuria*-containing composition to the surface of a seed, thus preventing or at least reducing unwanted spore drop-offs. Preferably, the adherent is non-toxic, biodegradable, and adhesive. Suitable adherents include, but are not limited to glues; polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. Additional suitable adherents are described in, for example, U.S. Pat. No. 7,213,367. In a specific embodiment, the adherent is polyvinyl acetate.

In another embodiment, the subject composition further comprises one or more polymers capable of mixing or attaching the active ingredient to a solid carrier. Suitable polymers may be natural or synthetic, and preferably have no or little phytotoxic effect on the seed to be coated. The polymer may be selected from, for example, polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

In another embodiment, the subject composition may further comprise a filler agent for protecting the seeds during stress conditions. In addition, the subject composition may further comprise a plasticizer to improve the fluidity of the liquid or semi-liquid composition, the flexibility of the mix or the polymeric composition, and/or the adhesiveness of the composition to the seed. In addition, it may be desirable to add to the formulation a drying agent such as calcium carbonate, kaolin or bentonite clay, perlite, diatomaceous earth or any other adsorbent material as described for example in U.S. Pat. No. 5,876,739. The skilled artisan, having the benefit of the current disclosure, can readily select desirable components to use in the formulation.

In yet a further embodiment, the subject *Pasteuria* composition comprises a second agriculturally beneficial ingredient. The second agriculturally beneficial ingredient could be, for example, selected from pesticides and fungicides, such as captan, thiram, metalaxyl, fludioxonil, oxadixyl, and isomers of each of those materials, and the like; herbicides, including compounds such as carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives.

The second agriculturally beneficial ingredient may further comprise fertilizers and/or ingredients that promote seed germination, and/or plant growth and/or health. In addition, it may comprise various bio-control agents such as other naturally-occurring or recombinant bacteria and fungi from the genera *Rhizobium, Bacillus, Pseudomonas, Serratia, Trichoderma, Glomus, Gliocladium* and mycorrhizal fungi. These chemical or biological agents may be beneficial for controlling nematode and/or other pests.

In light of the above teachings, one skilled in the art would include various ingredients such as inert or inactive ingredients, pesticides, or fertilizers into the subject composition and/or treatment method. In addition, one skilled in the art would typically not include those ingredients that would significantly harm the survival, growth, and/or reproduction of *Pasteuria* spores, reduce the ability of *Pasteuria* spores to attach to, infect, grow in, and/or kill nematodes, and/or inhibit the germination of seeds, plant growth, fruit growth and/or plant reproduction.

Plant Species

The materials and methods of the subject invention can be used for reducing damage to plant species, including, but not limited to, green beans, turf grasses, tomatoes, cotton, corn, soy beans, vegetables, wheat, barley, rice and canola.

Nematode Species

The materials and methods of the subject invention are useful for killing, controlling, and/or infecting nematodes; retarding the growth or reproduction of nematodes; reducing nematode population; and/or reducing or retarding damage to plants caused by phytopathogenic nematodes, plant-parasitic nematodes, and other soil-dwelling nematodes, including but not limited to *Meloidogyne arenaria, Pratylenchus brachyurus, Rotylenchulus reniformis,* and *Belonolaimus longicaudatus, Heterodera glycines* and *Hoplolaimus galeatus.*

Methods of Attachment and Delivery

The present invention also provides methods for attaching the *Pasteuria* composition to plant seeds and delivering the seeds to a situs of nematode infection.

It is preferable that the attachment method does not significantly harm the survival, growth, and/or reproduction of *Pasteuria* spores, reduce the ability of *Pasteuria* spores to attach to, infect, grow in, and/or kill nematodes. Preferably, the attachment and delivery methods would produce little phytotoxicity, such as affecting seed germination, plant vascularization, plant height, plant reproduction and/or fruit growth.

In certain embodiments, the *Pasteuria* composition is attached by coating, spraying, contacting, or mixing the seed with the *Pasteuria* composition. In one embodiment, the *Pasteuria* composition is attached by coating at least part of the surface area of the seed with the *Pasteuria* composition.

The subject composition can be attached to seeds using any of a variety of techniques, such as, for example, fluidized bed techniques, the roller mill methods, and spouted bed techniques. In addition, the subject composition can be attached to seeds using a machine, such as a rotostatic seed treater or a drum coater. The seeds may be pre-sized before coating. After coating, the seeds are typically dried and then transferred to a sizing machine for sizing, as is known in the art.

In one embodiment, the subject *Pasteuria* composition is first mixed with various agriculturally beneficial ingredients such as pesticides, herbicides, fungicides, fertilizers and/or various bio-control agents; and the mixture is then delivered to the seeds. In another embodiment, the subject *Pasteuria* composition is delivered sequentially with various agriculturally beneficial ingredients to the seeds. In another embodiment, the subject *Pasteuria* composition is delivered simultaneously with various agriculturally beneficial ingredients, but to different areas of the seed surface.

As used herein, seed coating includes any process that adds materials to the seed, including but not limited to, film coating, deposition of a single layer or layers of materials to the entire or part of the surface area of a seed, application of continuous layers of materials to the entire or part of the surface area of a seed, application of materials to the seed simultaneously or sequentially to cover the entire or part of the surface area of a seed.

In specific embodiments, the subject formulation can be coated on seeds using a variety of methods, including but not limited to, film coating, mixing seeds with the subject formulation in a container (e.g., a bottle or bag), mechanical application, tumbling, spraying, and immersion. A variety of active or inert materials can be used for coating, such as for example conventional film-coating materials including but not limited to water-based film coating materials such as SEPIRET (Seppic, Inc., Fairfield, N.J.) and Opacoat (Berwind Pharm. Services, Westpoint, Pa.).

Various methods for producing coated seeds further include those described in for example, U.S. Pat. Nos. 5,918, 413; 5,891,246; 5,554,445; 5,389,399; 5,107,787; 5,080,925; 4,759,945; 4,465,017; 5,939,356; 5,882,713; 5,876,739; 5,849,320; 5,834,447; 5,791,084; 5,661,103; 5,622,003; 5,580,544; 5,328,942; 5,300,127; 4,735,015; 4,634,587; 4,383,391; 4,372,080; 4,339,456; 4,272,417; and 4,245,432.

In another specific embodiment, the *Pasteuria* composition is delivered to seeds by solid matrix priming. To briefly illustrate, *Pasteuria* spores uniformly distributed in a solid matrix are placed in contact with seeds for a sufficient amount of time until the entire surface area of the seeds is covered with *Pasteuria* spores. The treated seeds can be separated from the solid matrix for further storage or use; or, alternatively, the treated seeds can be stored or planted together with the solid matrix.

Materials suitable for use as a solid matrix include polyacrylamide, starch, clay, silica, alumina, soil, sand, polyurea, polyacrylate, or any material capable of absorbing and releasing the subject composition onto seeds in a controlled manner. Preferably, the solid matrix is capable of releasing the subject composition in a controlled manner. The desired release rate may vary depending on the plant species, the *Pasteuria* species, the nematode species and other factors. Preferably, the subject composition can be released from the treated seeds at slow rate, such as by diffusion or moving through the matrix to the surrounding medium or the soil.

Seeds coated with the *Pasteuria* composition can be further enveloped with an additional thin film of over-coating to protect the *Pasteuria* coating. Exemplified techniques for over-coating include, but are not limited to, the fluidized bed technique and the drum film coating technique.

In a further embodiment, the delivery methods include an additional heat-treatment step. The heat-treatment step would enhance the nematicidal effect of the *Pasteuria* composition. In one embodiment, the *Pasteuria* spore suspension is heated before mixing with a solid carrier such as granules. In another embodiment, the *Pasteuria*-granule mixture is heated.

In addition, the subject method can comprise a step of applying an adherent to the seeds prior to or simultaneously with the *Pasteuria* treatment. In one embodiment, the seeds are first coated with a layer of adherent, and then treated with the *Pasteuria* composition. Suitable adherents include but are not limited to polyvinyl acetate, polyvinyl acetate copolymers, polyvinyl alcohol, polyvinyl alcohol copolymer, methyl cellulose, hydroxymethyl cellulose, hydroxymethyl propyl cellulose dextrin, alginate, molasse, polyvinyl pyrrolidone, polysaccharides, protein, fat, oil, polysaccharide, gum Arabic, gelatin, syrups, and any of the combination thereof.

In a specific embodiment, the subject method comprises a) mixing a *Pasteuria* spore suspension with a particulate carrier, and drying the mixture for a sufficient time until spore/granule particles are formed; b) coating seeds with an adherent; and c) contacting the seeds with the spore/granule particles until the seed is coated with a nematicidally-effective amount of the *Pasteuria* spores.

In yet a further embodiment, seeds treated with the subject *Pasteuria* composition can undergo additional processing steps such as drying. Advantageously, *Pasteuria* spores would not be damaged by drying. Thus, seeds treated with the subject composition can be stored for a prolonged period of time at room temperature. The long shelf life of the treated seeds also allows for variations in planting schedules. Advantageously, the survival rate of the *Pasteuria* spores is much higher than the survival rate of the vegetative form of the bacteria during transport, sowing, or once placed in the soil with seeds.

Although the seed treatments can be applied to a seed in any physiological state, it is preferred that the seed is in a sufficiently durable state so that the treatment process will produce little or no damage to the seed. Typically, the plant has been harvested from the field; the seed removed from the plant; and separated from any non-seed plant material. The seed is preferably biologically stable to the extent that the treatment does not cause damage to the seed. In one embodiment, for example, the treatment can be applied to seed corn that has been harvested, cleaned and dried to moisture content below about 15% by weight.

In an alternative embodiment, the seed can be one that has been dried and then primed with water and/or other materials and then re-dried before or during the treatment with the *Pasteuria* composition. The treatment can be applied to seeds at any time from harvest to sowing. As used herein, the term "unsown seed" includes any seed at any period from harvest to sowing.

Following are examples, which illustrate procedures for practicing the invention. These examples should not be construed as limiting. All percentages are by weight and all solvent mixture proportions are by volume unless otherwise noted.

Example 1

Preparation of *Pasteuria* Seed Coating

This Example illustrates methods for coating seeds with *Pasteuria penetrans* spores. *Pasteuria* spores are suspended in 10 mmol/L phosphate buffer and adjusted to about $2 \times 10^7$ spores/ml. A *Pasteuria*-granular mixture is obtained by mixing 5 ml of the spore suspension with 2 g AXIS® diatomaceous earth granules in a petri dish; or alternatively, by mixing 3 ml spore suspension with 2 g PROFILE® greens grade clay granules in a petri dish.

The mixture is dried under a lamp. Then, green bean seeds are treated with polyvinyl acetate and allowed to dry for 5 minutes in a flat dish. The seeds are thoroughly coated with the *Pasteuria*-granular mixture.

The *Pasteuria* coated seeds are suitable for immediate use or long term storage.

Example 2

Efficacy of *Pasteuria*-Coating of Seeds for Nematode Control

To evaluate the effect of *Pasteuria*-coated seeds on nematodes, a greenhouse pot test is performed.

2.2 g each of Axis turf supplement and Profile turf supplement were placed in separate petri dishes. *Pasteuria penetrans* spores at a concentration of $1.8 \times 10^7$ sp/ml were pipetted into each dish until the materials were saturated. The Axis supplement was saturated at 5 mL and the Profile was saturated at 4 mL. The dishes were set under a halogen lamp to dry. Green bean seeds (Ferry-Morse Blue Lake 274) were weighed and determined to have an average weight of 413.3 mg. Seeds were coated with a polyvinyl acetate sticker by pouring Elmer's Clear School Glue into a beaker and manually dunking individual seeds with tweezers into the glue. Seeds were dried for 5 minutes in a petri dish, then rolled in the spore-treated Axis and Profile granules until thoroughly coated. Control seeds were coated as above with untreated Axis and Profile granules.

The coated seeds are exposed, as follows, to field-collected root-knot nematodes for 21 days. In the control, non-treated green bean seeds are exposed to nematodes under the same conditions.

Styrofoam cups were filled with 1 kg of soil. Each pot was inoculated with 1500-2000 root-knot juveniles (*Meloidogyne arenaria*) by pipetting a suspension of the nematodes into the soil at a depth of 2 inches below the soil surface. The resulting hole was filled, then the green bean seeds were planted, one per pot, at a depth of 0.5 inches below the surface. 5 test (with spores) and 5 control seeds were planted. Pots were watered with 50 ml tap water daily, and maintained in the greenhouse until temperature readings indicated the nematodes had reached 500 degree-days.

Soil was then sampled for nematode counts, and plants and root systems removed from soil. Plant health and vigor was evaluated on a scale of 1-10, 1 being the least healthy and 10 the most healthy. Percent attachment was evaluated by recording the number of juvenile nematodes in a soil sample with 1 or more *Pasteuria* spores attached and calculating the percentage. Nematode eggs were counted by collecting egg masses from the root systems and counting the eggs microscopically.

Figure 2:
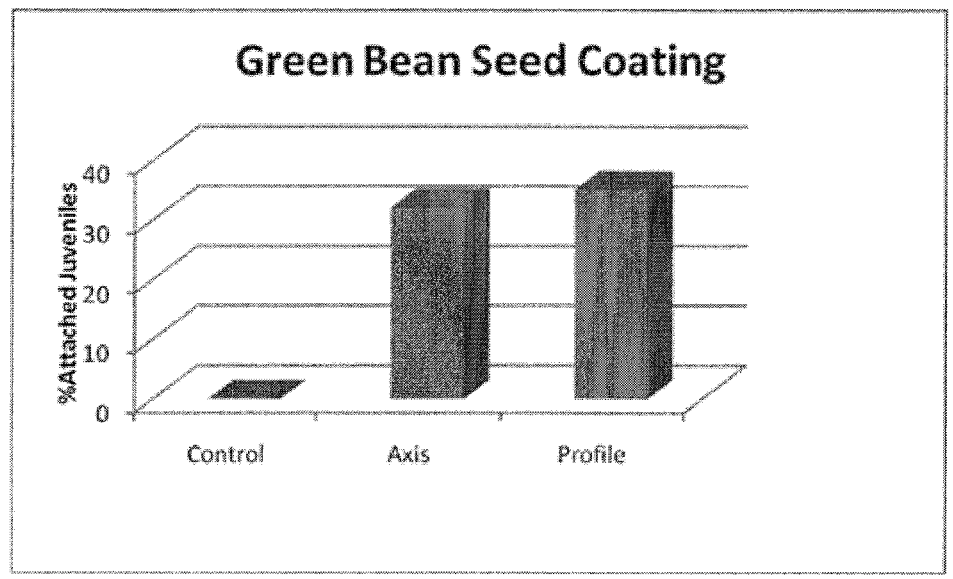
FIG. 2 shows the attachment of *Pasteuria* spores to nematodes in the soil.
Figure 3:
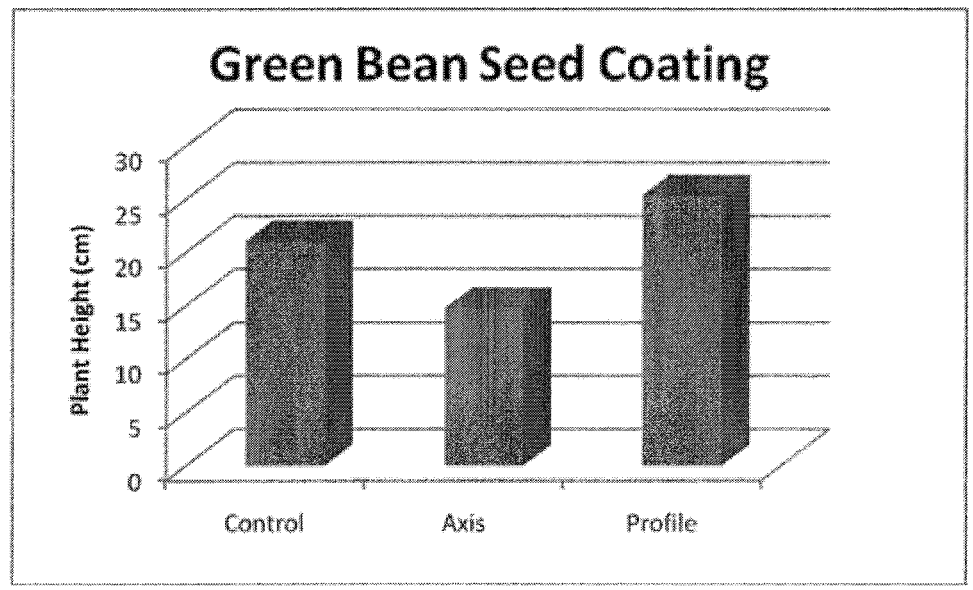
FIG. 3 shows the height of plants grown from seeds coated with *Pasteuria* for nematode control.

The results, shown in FIGS. 1 through 3, demonstrate that *Pasteuria* coating of seeds promotes seed emergence, plant height, and plant growth compared to the control treatment.

All references, including patents, patent applications, provisional applications, and publications referred to or cited herein are incorporated by reference in their entirety, including all figures and tables, to the extent they are not inconsistent with the explicit teachings of this specification.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method for controlling phytopathogenic and/or soil-dwelling nematodes, comprising attaching, to a green bean seed or soybean seed, a *Pasteuria* composition comprising an effective amount of *Pasteuria* spores; and planting the green bean seed or soybean seed;
   wherein an adherent has been applied to the green bean seed or soybean seed, and wherein the adherent is selected from the group consisting of polyvinyl alcohol, polyvinyl alcohol copolymer, methyl cellulose, hydroxymethyl cellulose, hydroxymethyl propyl cellulose dextrin, alginate, polyvinyl pyrrolidone, protein, fat, oil, and any combination thereof; and
   wherein the *Pasteuria* composition, when applied to the green bean seed or soybean seed, is present at a concentration ranging from about $1 \times 10^6$ to $1 \times 10^{12}$ spores per seed.

2. The method, according to claim 1, wherein the *Pasteuria* composition, when applied to the green bean seed or soybean seed, is present at a concentration ranging from about $1 \times 10^6$ to $1 \times 10^9$ spores per seed.

3. The method, according to claim 1, wherein the *Pasteuria* composition further comprises a liquid or solid carrier.

4. The method, according to claim 3, wherein the solid carrier is selected from the group consisting of dry powders, wettable powders, wettable granules, dry granules, particles, polymeric matrices, and slurries.

5. The method, according to claim 4, wherein the solid carrier comprises granules.

6. The method, according to claim 4, wherein the solid carrier is a polymeric matrix selected from the group consisting of polyacrylamide, starch, clay, silica, alumina, soil, sand, polyurea, polyacrylate, and any combination thereof.

7. The method, according to claim 1, wherein the *Pasteuria* spores comprise spores of *Pasteuria* species selected from the group consisting of *Pasteuria penetrans, Pasteuria ramose, Pasteuria thornei, Pasteuria nishizawae*, and any combination thereof.

8. The method, according to claim 1, wherein the phytopathogenic and/or soil-dwelling nematodes are selected from the group consisting of *Meloidogyne arenaria, Pratylenchus brachyurus, Rotylenchulus reniformis, Belonolaimus longicaudatus*, and any combination thereof.

9. The method, according to claim 1, wherein the seed further comprises a second agriculturally beneficial ingredient selected from the group consisting of pesticides, herbicides, fungicides, fertilizers, and bio-control agents.

10. The method, according to claim 1, wherein the *Pasteuria* spores comprise spores of *Pasteuria nishizawae*.

11. A green bean seed or soybean seed having at least part of the surface area coated with a *Pasteuria* composition, wherein the *Pasteuria* composition comprises an effective amount of *Pasteuria* spores for nematode control, and an adherent that has been applied to the green bean seed or soybean seed, and wherein the adherent is selected from the group consisting of polyvinyl alcohol, polyvinyl alcohol copolymer, methyl cellulose, hydroxymethyl cellulose, hydroxymethyl propyl cellulose dextrin, alginate, polyvinyl pyrrolidone, protein, fat, oil, and any combination thereof; and
   wherein the *Pasteuria* composition is present at a concentration ranging from about $1 \times 10^6$ to $1 \times 10^{12}$ spores per seed.

12. The green bean seed or soybean seed, according to claim 11, wherein the *Pasteuria* spores comprise spores of *Pasteuria nishizawae*.

13. The green bean seed or soybean seed, according to claim 11, wherein the *Pasteuria* composition is present at a concentration ranging from about $1 \times 10^6$ to $1 \times 10^9$ spores per seed.

14. A method for controlling phytopathogenic and/or soil-dwelling nematodes, comprising attaching, to a green bean seed or soybean seed, a *Pasteuria* composition comprising an effective amount of *Pasteuria* spores; and planting the green bean seed or soybean seed; wherein the *Pasteuria* composition, when applied to the green bean seed or soybean seed, is present at a concentration ranging from about $1 \times 10^6$ to $1 \times 10^{12}$ spores per seed.

15. The method, according to claim 14, wherein the *Pasteuria* composition further comprises a liquid or solid carrier.

16. The method, according to claim 15, wherein the solid carrier is selected from the group consisting of dry powders, wettable powders, wettable granules, dry granules, particles, polymeric matrices, and slurries.

17. The method, according to claim 15, wherein the solid carrier is a polymeric matrix selected from the group consisting of polyacrylamide, starch, clay, silica, alumina, soil, sand, polyurea, polyacrylate, and any combination thereof.

18. The method, according to claim 14, wherein the *Pasteuria* composition further comprises a polymer selected from the group consisting of ethylene vinyl acetate (EVA) copolymer, polyvinyl alcohol, polyvinyl alcohol copolymer, polyvinylpyrolidone, fat, oil, protein, vinylidene chloride, vinylidene chloride copolymer, calcium lignosulfonate, acrylic copolymer, polyvinylacrylate, polyethylene oxide, acrylamide polymer, acrylamide copolymer, polyhydroxyethyl acrylate, and polychloroprene.

19. The method, according to claim 14, wherein the *Pasteuria* spores comprise spores of *Pasteuria nishizawae*.

20. The method, according to claim 14, wherein the *Pasteuria* composition, when applied to the green bean seed or soybean seed, is present at a concentration ranging from about $1 \times 10^6$ to $1 \times 10^9$ spores per seed.

21. A green bean seed or soybean seed having at least part of the surface area coated with a *Pasteuria* composition, wherein the *Pasteuria* composition comprises an effective amount of *Pasteuria* spores for nematode control, wherein the *Pasteuria* composition is present at a concentration ranging from about $1 \times 10^6$ to $1 \times 10^{12}$ spores per seed.

22. The green bean seed or soybean seed, according to claim 21, wherein the *Pasteuria* composition further comprises a liquid or solid carrier.

23. The green bean seed or soybean seed, according to claim 22, wherein the solid carrier is a polymeric matrix selected from the group consisting of polyacrylamide, starch, clay, silica, alumina, soil, sand, polyurea, polyacrylate, and any combination thereof.

24. The green bean seed or soybean seed, according to claim 21, wherein the *Pasteuria* spores comprise spores of *Pasteuria nishizawae*.

25. The green bean seed or soybean seed, according to claim 21, wherein the *Pasteuria* composition is present at a concentration ranging from about $1 \times 10^6$ to $1 \times 10^9$ spores per seed.

* * * * *